(12) United States Patent
Nakamura et al.

(10) Patent No.: US 7,202,274 B2
(45) Date of Patent: Apr. 10, 2007

(54) CYCLIC HEMIACETAL DERIVATIVE AND USE THEREOF

(75) Inventors: Masayuki Nakamura, Kobe (JP); Jun Inoue, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 183 days.

(21) Appl. No.: 10/507,831

(22) PCT Filed: Mar. 14, 2003

(86) PCT No.: PCT/JP03/03122

§ 371 (c)(1), (2), (4) Date: Sep. 15, 2004

(87) PCT Pub. No.: WO03/078415

PCT Pub. Date: Sep. 25, 2003

(65) Prior Publication Data

US 2005/0119499 A1    Jun. 2, 2005

(30) Foreign Application Priority Data

Mar. 15, 2002 (JP) ............................. 2002-072762

(51) Int. Cl.
  *A61K 31/341* (2006.01)
  *C07D 307/20* (2006.01)
  *C07D 307/22* (2006.01)

(52) U.S. Cl. ...................... 514/472; 549/475

(58) Field of Classification Search ................ 549/475; 514/472
See application file for complete search history.

(56) References Cited

U.S. PATENT DOCUMENTS 5,496,834 A    3/1996  Sohda et al.
6,057,290 A    5/2000  Fukiage et al.

FOREIGN PATENT DOCUMENTS

| EP | 0 641 563 A1 | 3/1995 |
|----|---|---|
| EP | 0 641 800 | 3/1995 |
| EP | 0 810 221 A1 | 12/1997 |
| JP | B-6-29229 | 2/1994 |
| JP | 9-169752 | 6/1997 |
| WO | 98/04539 | 2/1998 |

OTHER PUBLICATIONS

"Inactivation of Calpain by Peptidyl Fluoromethyl Ketones", J. Med. Chem., vol. 35, pp. 216-220, (1992).

"Isosterism and Molecular Modification in Drug Design", C.W. Thornber, Imperial Chemical Industries Limited, Chem. Soc. Reviews, 8(4), pp. 563-580, (1979).

"Calpain inhibition: an overview of its therapeutic potential", Trends in Pharmacological Sciences, vol. 15, pp. 412-419, (1994).

"Cysteine protease inhibitor E64 reduces the rate of formation of selenite cataract in the whole animal", Curr. Eye Research, vol. 10, pp. 657-666, (1991).

*Primary Examiner*—Taofiq Solola
(74) *Attorney, Agent, or Firm*—Wenderoth, Lind & Ponack, L.L.P.

(57) ABSTRACT

A compound represented by the following formula (I)

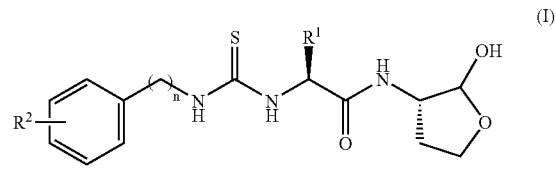

wherein $R^1$ is a lower alkyl group, $R^2$ is a hydrogen, a halogen, a cyano group, a lower alkyl group or a lower alkoxy group, and n is 0 or 1, which has a calpain inhibitory activity, is provided.

8 Claims, 3 Drawing Sheets

CYCLIC HEMIACETAL DERIVATIVE AND USE THEREOF

This application is a U.S. National Stage of International Application No. PCT/JP03/03122 filed Mar. 14, 2003.

TECHNICAL FIELD

The present invention relates to a novel cyclic hemiacetal derivative having a calpain inhibitory activity. More particularly, the present invention relates to a medicine containing a novel cyclic hemiacetal derivative.

BACKGROUND ART

Calpain is one of the proteolytic enzymes in cytoplasm, which are distributed widely in living organisms, and activated by a calcium ion. At present, it has been clarified that abnormal activation of this calpain is involved in various diseases such as stroke, subarachnoid hemorrhage, Alzheimer's disease, ischemic disease, muscular dystrophy, cataract, platelet aggregation, arthritis and the like [Trends in Pharmacological Sciences, vol. 15, p. 412 (1994)]. On the other hand, it has been clarified that a calpain inhibitor is effective for maintaining transparency of a lens in an experimental cataract model by way of lens culture [Curr. Eye Res., vol. 10, pp. 657–666 (1991)], and useful as a therapeutic agent for cataract (WO93/23032) and the like. As calpain inhibitors reported heretofore, peptide halomethane derivative (JP-B-6-29229), peptide diazomethane derivative [Biochem. J., vol. 253, pp. 751–758 (1988), J. Med. Chem., vol. 35, pp. 216–220 (1992)], peptidyl aldehyde derivative (EP771565, U.S. Pat. No. 6,057,290 and the like) and the like can be mentioned. However, as the situation stands, these inhibitors have not been put to practice.

DISCLOSURE OF THE INVENTION

The invention aims to provide a compound having a calpain inhibitory activity.

The present inventors have conducted intensive studies in an attempt to solve the above-mentioned problems, created a compound having a strong calpain inhibitory activity, and further studied to complete the present invention.

Accordingly, the present invention relates to (1) a compound represented by the formula (I)

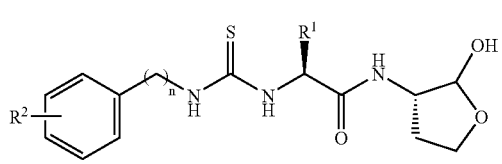

wherein $R^1$ is a lower alkyl group, $R^2$ is a hydrogen, a halogen, a cyano group, a lower alkyl group or a lower alkoxy group, and n is 0 or 1, (2) the compound of the above-mentioned (1), wherein $R^1$ is a lower alkyl group having 3 or 4 carbon atoms, (3) the compound of the above-mentioned (1) or (2), wherein $R^1$ is a group selected from isopropyl, isobutyl and sec-butyl, (4) the compound of the above-mentioned (1), wherein $R^1$ is isobutyl and $R^2$ is a group selected from a hydrogen, a halogen, a cyano group, a lower alkyl group and a lower alkoxy group, (5) (2S)-4-methyl-2-(((phenylamino)thioxomethyl)amino)-N-((3S)-tetrahydro-2-hydroxy-3-furanyl)pentanamide, (6) a medicine comprising a compound represented by of the formula (I)

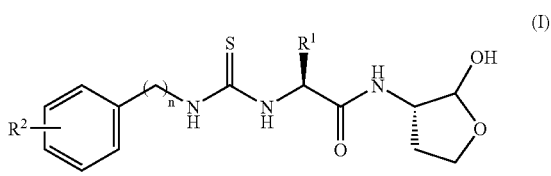

wherein $R^1$ is a lower alkyl group, $R^2$ is a hydrogen, a halogen, a cyano group, a lower alkyl group or a lower alkoxy group, and n is 0 or 1, (7) the medicine of the above-mentioned (6), which is a calpain inhibitor, (8) the medicine of the above-mentioned (6), which is an agent for the prophylaxis or treatment of a disease in which calpain is involved, (9) a pharmaceutical composition comprising a compound represented by the formula (I)

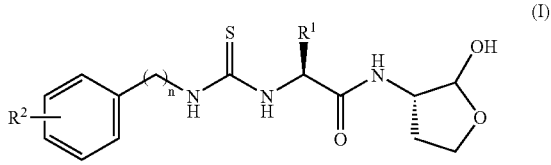

wherein $R^1$ is a lower alkyl group, $R^2$ is a hydrogen, a halogen, a cyano group, a lower alkyl group or a lower alkoxy group, and n is 0 or 1, and a pharmaceutically acceptable carrier,

(10) the pharmaceutical composition of the above-mentioned (9), which is a calpain inhibitor,

(11) a method for treating a disease in which calpain is involved, which comprises administering an effective amount of a compound represented by the formula (I)

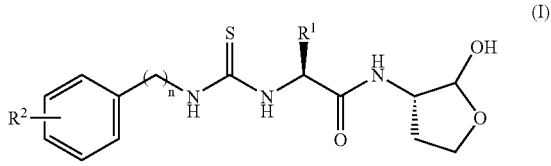

wherein $R^1$ is a lower alkyl group, $R^2$ is a hydrogen, a halogen, a cyano group, a lower alkyl group or a lower alkoxy group and n is 0 or 1, to a mammal in need of a treatment, and

(12) use of a compound represented by the formula (I)

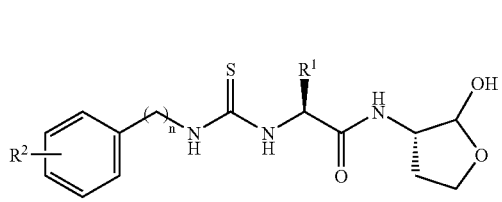

wherein $R^1$ is a lower alkyl group, $R^2$ is a hydrogen, a halogen, a cyano group, a lower alkyl group or a lower alkoxy group and n is 0 or 1, as a calpain inhibitor.

In the above-mentioned formula (I), a lower alkyl group represented by $R^1$ is a linear or branched alkyl group having 1 to 4 carbon atoms, such as methyl, ethyl, propyl, isopropyl, butyl, isobutyl, sec-butyl, tert-butyl and the like. It is preferably a lower alkyl group having 3 or 4 carbon atoms, more preferably isopropyl, isobutyl or sec-butyl, particularly preferably isobutyl. In the above-mentioned formula (I), as the halogen represented by $R^2$, fluorine, chlorine, bromine and iodine, particularly preferably fluorine, can be mentioned. In the above-mentioned formula (I), as the lower alkyl group represented by $R^2$, those similar to the aforementioned lower alkyl group represented by $R^1$ can be mentioned, and particularly preferred is methyl. In the above-mentioned formula (I), the lower alkoxy group represented by $R^2$ is a linear or branched alkoxy group having 1 to 4 carbon atoms, such as methoxy, ethoxy, propoxy, isopropoxy, butoxy, isobutoxy, sec-butoxy and tert-butoxy and the like, particularly preferably methoxy.

Moreover, the present invention encompasses compounds represented by the formula (I) (hereinafter sometimes to be referred to as the compound of the present invention) and also various solvates, substances having crystalline polymorphism and prodrugs of the compound of the present invention.

The compound of the present invention can be prepared by, for example, the following scheme:

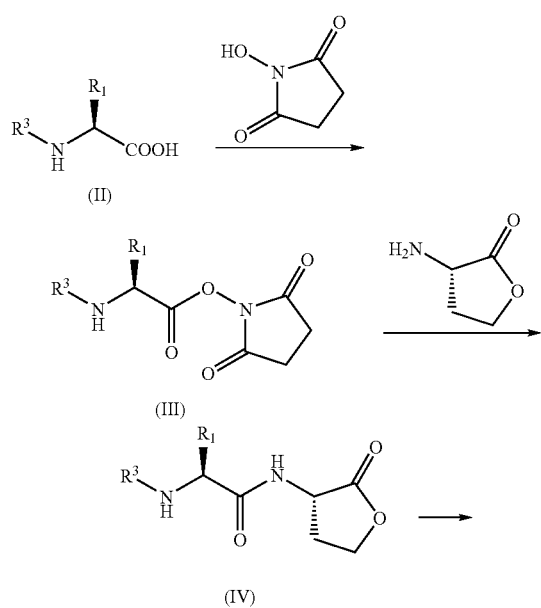

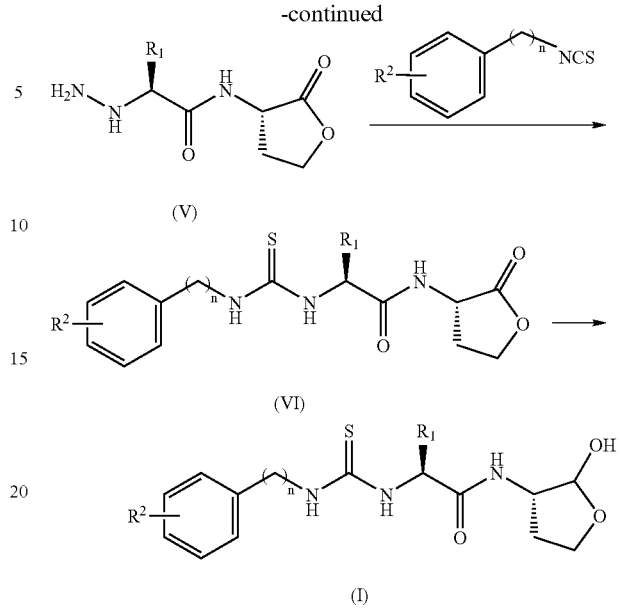

wherein each symbol is as defined above. The compounds represented by the formula (II) (hereinafter sometimes to be referred to as Compound (II)) are α-amino acids wherein an amino group is protected by a protecting group represented by $R^3$. As the protecting group represented by $R^3$, for example, those generally used in the field of peptide synthesis such as tert-butoxycarbonyl group (hereinafter sometimes to be referred to as Boc group), benzyloxycarbonyl group and the like can be mentioned.

The compounds represented by the formula (III) (hereinafter sometimes to be referred to as Compound (III)) can be obtained by dissolving Compound (II) and N-hydroxysuccinimide in an organic solvent generally used and stirring the resulting solution in the presence of a condensation agent. As the organic solvent generally used, for example, conventional solvents that do not adversely influence the reaction, such as tetrahydrofuran, dichloromethane, N,N-dimethylformamide, ethyl acetate and the like, and mixed solvents thereof can be mentioned, with preference given to dichloromethane. As the condensation agent, for example, 1-ethyl-3-(3-dimethylaminopropyl)carbodiimide hydrochloride, N,N-dicyclohexylcarbodiimide and the like are preferably used. The reaction temperature is generally under cooling, room temperature or under heating, and preferably in the range of from under ice-cooling to room temperature.

The compounds represented by the formula (IV) (hereinafter sometimes to be referred to as Compound (IV)) can be obtained by dissolving Compound (III) in an organic solvent generally used, adding α-amino-γ-butyrolactone or a salt thereof (hydrochloride or hydrobromide) thereto and stirring the mixture in the presence or absence of a base. As the organic solvent generally used, conventional solvents that do not adversely influence the reaction, such as N,N-dimethylformamide, dimethyl sulfoxide, tetrahydrofuran, dichloromethane, methanol, ethanol, benzene, toluene, ethyl acetate and the like, and mixed solvents thereof can be mentioned, with preference given to N,N-dimethylformamide. As the base, for example, trimethylamine, triethylamine, picoline, N-methylpyrrolidine, N-methylmorpholine, 1,5-diazabicyclo [4,3,0]non-5-en, 1,4-diazabicyclo[2,2,2]non-5-en, 1,8-diazabicyclo[5,4,0]-7-undecene and the like can be mentioned, with preference given to triethylamine. While the reaction temperature is not particularly limited, it is generally under cooling, room temperature or under heating, with preference given to the range of from under ice-cooling to room temperature.

The compounds represented by the formula (V) (hereinafter sometimes to be referred to as Compound (V)) can be obtained by appropriately selecting and applying a conventional method used for an elimination reaction of an amino protecting group for $R^3$, which is a protecting group of Compound (IV). For example, when a tert-butoxycarbonyl group is used as a protecting group, Compound (IV) is dissolved in an organic solvent generally used and stirring the resulting solution in the presence of an acid to eliminate $R^3$. As the organic solvent generally used, for example, conventional solvents that do not adversely influence the reaction, such as tetrahydrofuran, dichloromethane, ethyl acetate and the like, and mixed solvents thereof can be mentioned, with preference given to ethyl acetate. As the acid, hydrochloric acid, trifluoroacetic acid, p-toluenesulfonic acid and the like can be mentioned. It is also possible to use a commercially available solution of hydrochloric acid in ethyl acetate or dioxane and the like for the elimination. While the reaction temperature is not particularly limited, it is generally under cooling, room temperature or under heating, with preference given to the range of from under ice-cooling to room temperature. When a benzyloxycarbonyl group is used, a catalytic reduction is conducted in the presence of a conventional metal catalyst (e.g., palladium carbon, Raney-nickel, platinum oxide and the like). The hydrogen pressure is generally about 1 atm–about 50 atm, preferably about 1 atm–about 5 atm. As the solvent, alcohols (methanol, ethanol and the like), ethers (tetrahydrofuran and the like), organic acids (acetic acid and the like), and mixed solvents thereof can be used. The reaction temperature is not particularly limited as long as unpreferable side reactions do not occur, and the reaction is generally carried out under cooling, at room temperature or under heating. Compound (V) may be used for the next reaction without isolation or purification, as long as the next reaction is not influenced.

The compounds represented by the formula (VI) (hereinafter sometimes to be referred to as Compound (VI)) can be obtained by adding various isothiocyanate reagents to Compound (V) and stirring the mixture in an organic solvent generally used, in the presence or absence of a base. As the organic solvents generally used, for example, conventional solvents that do not adversely influence the reaction, such as tetrahydrofuran, dichloromethane, N,N-dimethylformamide, ethyl acetate and the like, and mixed solvents thereof can be mentioned, with preference given to ethyl acetate. As the base, for example, trimethylamine, triethylamine, picoline, N-methylpyrrolidine, N-methylmorpholine, 1,5-diazabicyclo[4,3,0]non-5-en, 1,4-diazabicyclo[2,2,2]non-5-en, 1,8-diazabicyclo[5,4,0]-7-undecene and the like can be mentioned, with preference given to triethylamine. While the reaction temperature is not particularly limited, the reaction is generally carried out under cooling, at room temperature or under heating, preferably in the range of from under ice-cooling to room temperature.

The compounds represented by the formula (I) can be obtained by subjecting Compound (VI) to a reduction reaction. This reduction reaction can be carried out by a method known per se, such as reduction with metal hydride, reduction with a hydrogen-metal complex compound, reduction with diborane or substituted borane, catalytic hydrogenation and the like. In other words, this reaction is carried out by treating Compound (VI) with a reduction agent. As the reduction agent, a hydrogen-metal complex compound such as alkali metal borohydride (e.g., sodium borohydride, lithium borohydride etc.), lithium aluminum hydride and the like, metal hydride such as sodium hydride and the like, a metal or a metal salt such as an organic tin compound (triphenyltin hydride etc.), a nickel compound, a zinc compound and the like, catalytic reduction agents using a transition metal catalyst (e.g., palladium, platinum, rhodium and the like) and hydrogen, and diborane, and the like can be mentioned. In particular, the reaction is advantageously carried out using diisobutyl aluminum hydride. This reaction is carried out in an organic solvent that does not influence the reaction. For example, conventional solvents that do not adversely influence the reaction, such as N,N-dimethylformamide, dimethyl sulfoxide, tetrahydrofuran, dichloromethane, methanol, ethanol, benzene, toluene, ethyl acetate and the like, and a mixed solvent thereof can be mentioned, with preference given to dichloromethane. The reaction temperature is about −100° C. to about 150° C., particularly preferably about −80° C. to about −10° C., and the reaction time is about 1–about 24 hr. The thus-obtained cyclic hemiacetal derivative can be isolated or purified by a known separation and purification means, such as concentration, concentration under reduced pressure, solvent extraction, crystallization, recrystallization, phase transfer, chromatography and the like.

As the compounds represented by the formula (I), which are prepared by the above-mentioned methods, for example, (2S)-4-methyl-2-(((phenylamino)thioxomethyl)amino)-N-((3S)-tetrahydro-2-hydroxy-3-furanyl)pentanamide, (2S)-3-methyl-2-(((phenylamino)thioxomethyl)amino)-N-((3S)-tetrahydro-2-hydroxy-3-furanyl)pentanamide, (2S)-3-methyl-2-(((phenylamino)thioxomethyl)amino)-N-((3S)-tetrahydro-2-hydroxy-3-furanyl)butanamide, (2S)-2-(((benzylamino)thioxomethyl)amino)-4-methyl-N-((3S)-tetrahydro-2-hydroxy-3-furanyl)pentanamide, (2S)-2-((((4-fluorophenyl)amino)thioxomethyl)amino)-4-methyl-N-((3S)-tetrahydro-2-hydroxy-3-furanyl)pentanamide, (2S)-2-((((4-methoxyphenyl)amino)thioxomethyl)amino)-4-methyl-N-((3S)-tetrahydro-2-hydroxy-3-furanyl)pentanamide, (2S)-2-((((3-cyanophenyl)amino)thioxomethyl)amino)-4-methyl-N-((3S)-tetrahydro-2-hydroxy-3-furanyl)pentanamide, (2S)-2-((((4-cyanophenyl)amino)thioxomethyl)amino)-4-methyl-N-((3S)-tetrahydro-2-hydroxy-3-furanyl)pentanamide, (2S)-4-methyl-2-((((2-methylphenyl)amino)thioxomethyl)amino)-N-((3S)-tetrahydro-2-hydroxy-3-furanyl)pentanamide, (2S)-4-methyl-2-((((3-methylphenyl)amino)thioxomethyl)amino)-N-((3S)-tetrahydro-2-hydroxy-3-furanyl)pentanamide, (2S)-4-methyl-2-((((4-methylphenyl)amino)thioxomethyl)amino)-N-((3S)-tetrahydro-2-hydroxy-3-furanyl)pentanamide and the like can be mentioned.

The compound of the present invention is a novel compound that has not been described in any reference and, since it has a superior calpain inhibitory activity as shown in Experimental Examples below, the compound is useful as a medicine as a calpain inhibitor obtained by combining the compound as an active ingredient with a below-mentioned carrier and the like as necessary. The structural formulas of the compounds disclosed in Examples mentioned below are shown in Table 1.

TABLE 1

Structural formula of Example compound

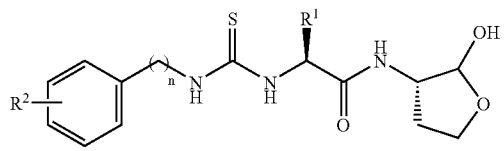

| Compound No. | n | R¹ | R² |
|---|---|---|---|
| 1 | 0 | isobutyl | H |
| 2 | 0 | sec-butyl | H |
| 3 | 0 | isopropyl | H |
| 4 | 1 | isobutyl | H |
| 5 | 0 | isobutyl | 4-fluoro |
| 6 | 0 | isobutyl | 4-methoxy |
| 7 | 0 | isobutyl | 3-cyano |
| 8 | 0 | isobutyl | 4-cyano |
| 9 | 0 | isobutyl | 2-methyl |
| 10 | 0 | isobutyl | 3-methyl |
| 11 | 0 | isobutyl | 4-methyl |

A medicine containing the compound of the present invention is useful as a pharmaceutical preparation for the prophylaxis or treatment of ischemic disease, immunity disease, Alzheimer's disease, osteoporosis, ischemic brain disease, cataract, glaucoma, retinal (choroidal) disease, complications of posterior segment of the eye arising from photocoagulation (e.g., macular edema, retinal detachment, optic neuritis, abnormal visual field, abnormal light sense, abnormal color vision and the like) and the like, or a drug for the prophylaxis or treatment of angiogenesis, retinal detachment and the like, in mammals (e.g., human, rat, mouse, rabbit, bovine, pig, dog, cat and the like). In addition, since the compounds of the present invention are mostly superior to the same kind of conventional compounds in water solubility, which makes it possible to use the inventive compound as an aqueous liquid conventionally difficult to provide. Moreover, the compound of the present invention is superior in penetration to tissue and absorbability, shows extremely low toxicity and is superior in safety.

A medicine containing the compound of the present invention can be administered systemically or topically. For systemic administration, it is administered orally or parenterally by intravenous injection, subcutaneous injection, intramuscular injection and the like. Topically, it is administered dermally, mucosally, intranasally, intraocularly and the like.

As a dosage form of a medicine containing the compound of the present invention, solid agents such as powder, granule, tablet, capsule, suppository and the like, liquids such as syrup, injection, eye drop, nose drop and the like, and the like can be mentioned. For preparation of granule or tablet, for example, any dosage form is available by the use of excipients (lactose, sucrose, glucose, starch, crystalline cellulose and the like), lubricants (magnesium stearate, talc, stearic acid, calcium stearate and the like), disintegrants (starch, carmellose sodium, calcium carbonate and the like), binders (starch liquid, hydroxypropyl cellulose liquid, carmellose liquid, gum arabic liquid, gelatin liquid, sodium alginate liquid and the like) and the like. For granule and tablet, a coating may be formed with a suitable coating agent (gelatin, sucrose, gum arabic, carnauba wax and the like), an enteric coating agent (e.g., cellulose acetate phthalate, methacrylic acid copolymer, hydroxypropyl cellulose phthalate, carboxymethylethylcellulose and the like) and the like.

For preparation of a capsule, suitable excipients, such as magnesium stearate, calcium stearate, talc, light anhydrous silicic acid and the like for improving fluidity and lubrication, crystalline cellulose, lactose and the like for compression fluidity, as well as the above-mentioned disintegrant and the like are appropriately added and uniformly admixed or processed into granules or a granular form, a coating is formed with a suitable coating agent, and the resulting product is filled in a capsule, or can be encapsulation formed with a capsule base obtained by adding glycerol, sorbitol and the like to a suitable capsule base (gelatin and the like) to increase plasticity. These capsules can contain a coloring agent, a preservative [sulfur dioxide, parabens (methyl p-hydroxybenzoate, ethyl p-hydroxybenzoate, propyl p-hydroxybenzoate)] and the like as necessary. Capsule can also be prepared into a conventional capsule, as well as an enteric coated capsule, an intragastric resistance capsule or a sustained release capsule. When an enteric capsule is to be prepared, a compound or a compound containing the above-mentioned suitable excipients, which has been coated with an enteric coating agent, is filled in a conventional capsule or a capsule itself may be coated with an enteric coating agent, or an enteric polymer may be used as a base to be formed.

When a suppository is to be prepared, a suppository base (e.g., cacao butter, macrogol and the like) can be appropriately selected and used.

When a syrup is to be prepared, for example, a stabilizer (disodium edetate and the like), a suspending agent (gum arabic, carmellose and the like), a corrigent (simple syrup, glucose and the like), an aromatic and the like can be appropriately selected and used.

When an injection, an eye drop or a nose drop is to be prepared, it can be prepared by dissolving or dispersing the compound in a solution appropriately containing a pharmaceutically acceptable additive, such as an isotonicity agent (sodium chloride, potassium chloride, glycerol, mannitol, sorbitol, boric acid, borax, glucose, propylene glycol and the like), a buffer (phosphate buffer, acetate buffer, borate buffer, carbonate buffer, citrate buffer, Tris buffer, glutamic acid, epsilon aminocaproic acid and the like), a preservative (p-hydroxybenzoic acid esters, chlorobutanol, benzyl alcohol, benzalkonium chloride, sodium dehydroacetate, disodium edetate, boric acid, borax and the like), a thickener (hydroxyethylcellulose, hydroxypropylcellulose, polyvinyl alcohol, polyethylene glycol and the like), a stabilizer (sodium bisulfite, sodium hyposulfite, disodium edetate, sodium citrate, ascorbic acid, dibutylhydroxytoluene and the like), a pH adjusting agent (hydrochloric acid, sodium hydroxide, phosphoric acid, acetic acid and the like) and the like.

Of the compounds of the present invention, a compound having suitable water-solubility desired as a pharmaceutical product can be advantageously used as a water-soluble liquid particularly for the above-mentioned pharmaceutical preparations such as syrup, injection, eye drop, nose drop and the like.

While the amount of the additive to be contained in the above-mentioned syrup, injection, eye drop or nose drop varies depending on the kind, use and the like of the additive to be used, it needs only to be added at a concentration capable of achieving the object of the additive, wherein an isotonicity agent is generally added at about 0.5–about 5.0 w/v % to make the osmotic pressure about 229–about 343 mOsm. A buffer is added at about 0.01–about 2.0 w/v %; a thickener is added at about 0.01–about 1.0 w/v %; and a stabilizer is added at about 0.001–about 1.0 w/v %. A pH adjusting agent is added as appropriate and generally adjusted to about pH 3–about 9, preferably about 4–about 8.

While the dose of the compound of the present invention varies depending on the target disease, condition, subject of administration, administration method and the like, for example, in the case of a medicine for internal use, a single dose of about 1–about 100 mg is administered to an adult several times a day, and in the case of an injection, about 0.1–about 30 mg is administered to an adult once a day. For topical administration to the eye, an eye drop containing about 0.001–about 1.0 w/v %, preferably about 0.01–about 0.5 w/v %, of the compound of the present invention is preferably distilled into the eye several times a day by about 20–about 50 μL for one distillation.

BEST MODE FOR EMBODYING THE INVENTION

Figure 1:
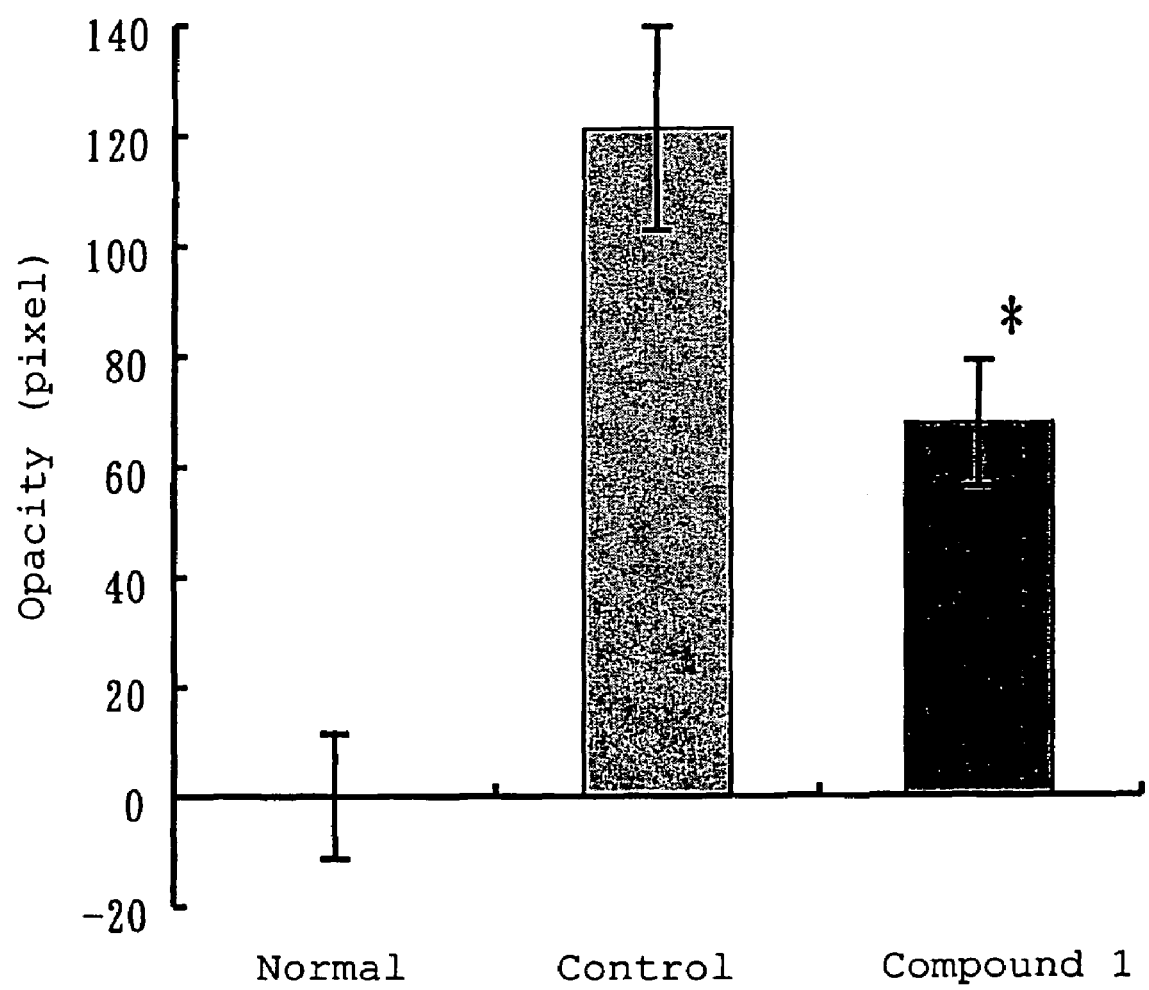
FIG. 1 is a graph showing a lens opacity preventive effect of Compound 1 in rat lens culture, wherein each value shows mean±standard error (n=5), and * shows a significant difference p<0.01 from the control group by the Student's T test (both sides).

The present invention is explained in more detail by referring to the following Reference Examples, Examples, Experimental Examples and Formulation Examples, which are not to be construed as limitative.

In the analysis values of the compound discussed in Examples, the melting point was measured using MP-500V (uncorrected) manufactured by Yanaco LID. Co., Ltd. The nuclear magnetic resonance spectrum (NMR) was measured using Gemini2000 manufactured by Varian. Inc. The NMR spectra of Compounds 1 to 11 were complicated due to the presence of anomeric carbon, and when a major peak and a minor peak of the same proton could be distinguished, they are described separately. The Matrix Assisted Laser Desorption Ionization-Time Of Flight Mass Spectrometry (MALDI-TOF MS) was measured using Voyager DE PRO manufactured by PerSeptive Biosystems, Inc. The specific rotation ($[\alpha]_D$) was measured using SEPA-2000 manufactured by Horiba, Ltd.

REFERENCE EXAMPLE 1

N-(tert-butoxy)carbonyl-L-leucine N-hydroxysuccinimide ester (Reference Compound 1)

Boc-L-leucine (27 g, 110 mmol) and N-hydroxysuccinimide (16 g, 140 mmol) were dissolved in tetrahydrofuran (180 mL). A suspension of 1-ethyl-3-(3-dimethylaminopropyl)carbodiimide hydrochloride (27 g, 140 mmol) in dichloromethane (180 mL) was added thereto under ice-cooling. This reaction mixture was stirred at room temperature for 18 hr and concentrated under reduced pressure. The residue was dissolved in ethyl acetate, and this solution was washed with 1M hydrochloric acid, saturated aqueous sodium hydrogen carbonate solution and saturated brine, dried over anhydrous magnesium sulfate, and concentrated under reduced pressure. The obtained solid was crystallized from hexane to give Reference Compound (33 g, 93%) as colorless crystals.

mp 74.1–75.5° C. $^1$H-NMR(300 MHz, DMSO-d$_6$)δ: 0.88 (d, 3H, J=6.3 Hz), 0.91 (d, 3H, J=6.3 Hz), 1.39 (s, 9H), 1.54–1.75 (m, 3H), 2.80 (s, 4H), 4.32 (m, 1H), 7.62 (d, 1H, J=8.4 Hz).

REFERENCE EXAMPLE 2

N-(tert-butoxy)carbonyl-L-isoleucine N-hydroxysuccinimide ester (Reference Compound 2)

Operations in the same manner as in Reference Example 1 and using Boc-L-isoleucine instead of 1 Boc-L-leucine afforded Reference Compound 2 as a white solid.

$^1$H-NMR (300 MHz, CDCl$_3$)δ: 0.97 (t, 3H, J=7.5 Hz), 1.04 (d, 3H, J=6.9 Hz), 1.26 (m, 1H), 1.45 (s, 9H), 1.60 (m, 1H), 1.98 (m, 1H), 2.83 (s, 4H), 4.62 (dd, 1H, J=8.7, 5.1 Hz), 5.01 (d, 1H, J=8.7 Hz).

REFERENCE EXAMPLE 3

N-(tert-butoxy)carbonyl-L-valine N-hydroxysuccinimide ester (Reference Compound 3)

Operations in the same manner as in Reference Example 1 and using Boc-L-valine instead of Boc-L-leucine afforded Reference Compound 3 as colorless crystals.

mp 125.7–127.4° C. $^1$H-NMR (300 MHz, DMSO-d$_6$)δ: 0.99 (d, 6H, J=6.9 Hz), 1.4 (s, 9H), 2.15 (m, 1H), 2.81 (s, 4H), 4.22 (dd, 1H, J=8.1, 6.6 Hz), 7.58 (d, 1H, J=8.4 Hz).

REFERENCE EXAMPLE 4

(2S)-2-((tert-butoxy)carbonylamino)-4-methyl-N-((3S)-tetrahydro-2-oxo-3-furanyl)pentanamide (Reference Compound 4)

Reference Compound 1 (20 g, 61 mmol) was dissolved in N,N-dimethylformamide (120 mL) and (S)-(−)-α-aminobutyrolactone hydrobromide (17 g, 91 mmol) and triethylamine (18 g, 180 mmol) were added under ice-cooling. This solution was stirred at room temperature for 18 hr. The reaction mixture was diluted with ethyl acetate, and this solution was washed with 1M hydrochloric acid, saturated aqueous sodium hydrogen carbonate solution and saturated brine, dried over anhydrous magnesium sulfate, and concentrated under reduced pressure. The residue was crystallized from hexane to give Reference Compound 4 (19 g, 99%) as colorless crystals.

mp 92.5–93.3° C. $^1$H-NMR (300 MHz, DMSO-d$_6$)δ: 0.85 (d, 3H, J=6.3 Hz), 0.88 (d, 3H, J=6.6 Hz), 1.28–1.50 (m, 2H), 1.38 (s, 9H), 1.61 (m, 1H), 2.14 (m, 1H), 2.39 (m, 1H), 3.96 (m, 1H), 4.20 (m, 1H), 4.34 (m, 1H), 4.60 (m, 1H), 6.88 (d, 1H, J=8.4 Hz), 8.30 (d, 1H, J=8.4 Hz).

REFERENCE EXAMPLE 5

(2S)-2-((tert-butoxy)carbonylamino)-3-methyl-N-((3S)-tetrahydro-2-oxo-3-furanyl)pentanamide (Reference Compound 5)

Operations in the same manner as in Reference Example 4 and using Reference Compound 2 instead of Reference Compound 1 afforded Reference Compound 5 as a white powder.

mp 156.4–159.2° C. $^1$H-NMR (300 MHz, CDCl$_3$)δ: 0.90 (t, 3H, J=7.5 Hz), 0.95 (d, 3H, J=6.6 Hz), 1.15 (m, 1H), 1.43 (S, 9H), 1.50 (m, 1H), 1.88 (m, 1H), 2.21 (m, 1H), 2.73 (m, 1H), 4.01 (m, 1H), 4.26 (m, 1H), 4.46 (td, 1H, J=9.0, 1.2 Hz), 4.54 (m, 1H), 5.11 (d, 1H, J=8.7 Hz), 6.87 (m, 1H).

REFERENCE EXAMPLE 6

(2S)-2-((tert-butoxy)carbonylamino)-3-methyl-N-((3S)-tetrahydro-2-oxo-3-furanyl)butanamide (Reference Compound 6)

Operations in the same manner as in Reference Example 4 and using Reference Compound 3 instead of Reference Compound 1 afforded Reference Compound 6 as colorless crystals.

mp 113.9–114.9° C. $^1$H-NMR (300 MHz, DMSO-d$_6$)δ: 0.84 (d, 3H, J=6.9 Hz), 0.87 (d, 3H, J=6.9 Hz); 1.38 (s, 9H), 1.93 (m, 1H), 2.17 (m, 1H), 2.39 (m, 1H), 3.78 (dd, 1H, J=8.9, 7.2 Hz), 4.21 (m, 1H), 4.40 (m, 1H), 4.60 (m, 1H), 6.68 (d, 1H, J=8.9 Hz), 8.37 (d, 1H, J=7.8 Hz).

REFERENCE EXAMPLE 7

(2S)-4-methyl-2-(((phenylamino)thioxomethyl)amino)-N-((3S)-tetrahydro-2-oxo-3-furanyl)pentanamide (Reference Compound 7)

Reference Compound 4 (3.4 g, 11 mmol) was dissolved in ethyl acetate (100 mL) and 4N hydrochloric acid/ethyl acetate solution (8.0 mL) was added under ice-cooling. This solution was stirred at room temperature for 18 hr (oil-down was confirmed), and the solvent was removed under reduced pressure. Thereto was added ethyl acetate and the solvent was again removed under reduced pressure (repeated twice). The residue was suspended in ethyl acetate, and phenyl isothiocyanate (1.5 g, 11 mmol) and triethylamine (3.3 g, 32 mmol) were added thereto. This solution was stirred at room temperature for 3 hr. The reaction mixture was washed with 1M hydrochloric acid, saturated aqueous sodium hydrogen carbonate solution and saturated brine, dried over anhydrous magnesium sulfate and concentrated under reduced pressure. The residue was crystallized from hexane, and washed with hexane to give Reference Compound 7 (1.8 g, 48%) as colorless crystals.

mp 77.7–78.8° C. $^1$H-NMR (300 MHz, DMSO-d$_6$)δ: 0.92 (d, 3H, J=6.3 Hz), 0.93 (d, 3H, J=6.6 Hz), 1.55–1.70 (m, 3H), 2.20 (m, 1H), 2.40 (m, 1H), 4.22 (m, 1H), 4.36 (m, 1H), 4.62 (m, 1H), 4.96 (m, 1H), 7.10 (m, 1H), 7.29–7.34 (m, 2H), 7.51–7.54 (m, 2H), 7.78 (d, 1H, J=8.1 Hz), 8.64 (d, 1H, J=8.1 Hz), 9.70 (s, 1H).

REFERENCE EXAMPLE 8

(2S)-3-methyl-2-(((phenylamino)thioxomethyl)amino)-N-((3S)-tetrahydro-2-oxo-3-furanyl)pentanamide (Reference Compound 8)

Operations in the same manner as in Reference Example 7 and using Reference Compound 5 instead of Reference Compound 4 afforded Reference Compound 8 as a white solid.

mp 71.9–72.7° C. $^1$H-NMR (300 MHz, CDCl$_3$)δ: 0.91 (t, 3H, J=7.4 Hz), 0.96 (d, 3H, J=6.7 Hz), 1.10–1.22 (m, 1H), 1.48–1.59 (m, 1H), 1.94–2.02 (m, 1H), 2.18–2.33 (m, 1H), 2.63–2.76 (m, 1H), 4.20–4.29 (m, 1H), 4.44 (t, 1H, J=9.0 Hz), 4.59 (ddd, 1H, J=7.2, 8.9, 11.3 Hz), 4.92 (t, 1H, J=7.5 Hz), 6.77 (brs, 1H) 6.98 (brs, 1H), 7.26–7.44 (m, 5H), 8.17 (brs, 1H).

REFERENCE EXAMPLE 9

(2S)-3-methyl-2-(((phenylamino)thioxomethyl)amino)-N-((3S)-tetrahydro-2-oxo-3-furanyl)butanamide (Reference Compound 9)

Operations in the same manner as in Reference Example 7 and using Reference Compound 6 instead of Reference Compound 4 afforded Reference Compound 9 as colorless crystals.

$^1$H-NMR (300 MHz, CDCl$_3$)δ: 0.97 (d, 3H, J=6.9 Hz), 1.00 (d, 3H, J=6.9 Hz), 1.75 (brs, 1H), 2.15–2.33 (m, 2H), 2.63–2.72 (m, 1H), 4.45 (t, 1H, J=9.0 Hz), 4.61 (ddd, 1H, J=11.4, 8.8, 7.3 Hz), 4.89 (t, 1H, J=7.4 Hz), 6.75 (d, 1H, J=8.1 Hz), 7.01 (d, 1H, J=6.7 Hz), 7.21–7.50 (m, 5H), 8.17 (brs, 1H).

REFERENCE EXAMPLE 10

(2S)-2-(((benzylamino)thioxomethyl)amino)-4-methyl-N-((3S)-tetrahydro-2-oxo-3-furanyl)pentanamide (Reference Compound 10)

Operations in the same manner as in Reference Example 7 and using benzyl isothiocyanate instead of phenyl isothiocyanate afforded Reference Compound 10 as a colorless oil.

$^1$H-NMR (300 MHz, DMSO-d$_6$)δ: 0.92 (d, 3H, J=6.0 Hz), 0.93 (d, 3H, J=6.0 Hz), 1.56–1.72 (m, 3H), 2.18 (m, 1H), 2.41 (m, 1H), 4.22 (m, 1H), 4.36 (m, 1H), 4.63 (m, 1H), 5.00 (m, 1H), 7.49–7.98 (m, 8H), 8.60 (d, 1H, J=8.1 Hz), 9.75 (s, 1H).

REFERENCE EXAMPLE 11

(2S)-2-((((4-fluorophenyl)amino)thioxomethyl)amino)-4-methyl-N-((3S)-tetrahydro-2-oxo-3-furanyl)pentanamide (Reference Compound 11)

Operations in the same manner as in Reference Example 7 and using 4-fluorophenyl isothiocyanate instead of phenyl isothiocyanate afforded Reference Compound 11 as pale-yellow crystals.

mp 47.5–48.4° C. $^1$H-NMR (300 MHz, DMSO-d$_6$)δ: 0.92 (d, 3H, J=6.3 Hz), 0.93 (d, 3H, J=6.3 Hz), 1.55–1.72 (m, 3H), 2.18 (m, 1H), 2.39 (m, 1H), 4.21 (m, 1H), 4.35 (m, 1H), 4.60 (m, 1H), 4.95 (m, 1H), 7.12–7.18 (m, 2H), 7.49–7.55 (m, 2H), 7.78 (d, 1H, J=7.8 Hz), 8.62 (d, 1H, J=7.8 Hz), 9.65 (s, 1H).

REFERENCE EXAMPLE 12

(2S)-2-((((4-methoxyphenyl)amino)thioxomethyl)amino)-4-methyl-N-((3S)-tetrahydro-2-oxo-3-furanyl)pentanamide (Reference Compound 12)

Operations in the same manner as in Reference Example 7 and using 4-methoxyphenyl isothiocyanate instead of phenyl isothiocyanate afforded Reference Compound 12 as pale-yellow crystals.

mp 44.5–46.1° C. $^1$H-NMR (300 MHz, DMSO-$d_6$)δ: 0.92 (d, 6H, J=6.6 Hz), 1.54–1.67 (m, 3H), 2.18 (m, 1H), 2.39 (m, 1H), 3.74 (s, 3H), 4.20 (m, 1H), 4.33 (m, 1H), 4.58 (m, 1H), 4.96 (m, 1H), 6.84–6.91 (m, 2H), 7.32–7.35 (m, 2H), 7.54 (d, 1H, J=8.4 Hz), 8.59 (d, 1H, J=8.1 Hz), 9.50 (s, 1H).

REFERENCE EXAMPLE 13

(2S)-2-((((3-cyanophenyl)amino)thioxomethyl)amino)-4-methyl-N-((3S)-tetrahydro-2-oxo-3-furanyl)pentanamide (Reference Compound 13)

Operations in the same manner as in Reference Example 7 and using 3-cyanophenyl isothiocyanate instead of phenyl isothiocyanate afforded Reference Compound 13 as a white solid.

mp 72.0–73.2° C. $^1$H-NMR (300 MHz, DMSO-$d_6$)δ: 0.92 (d, 3H, J=6.1 Hz), 0.92 (d, 3H, J=6.1 Hz), 1.56–1.72 (m, 3H), 2.11–2.25 (m, 1H), 2.36–2.44 (m, 1H), 4.17–4.26 (m, 1H), 4.35 (dt, 1H, J=8.8, 1.7 Hz), 4.57–4.66 (m, 1H), 4.93 (dd, 1H, J=14.2, 7.2 Hz), 7.49–7.53 (m, 2H), 7.71–7.77 (m, 1H), 8.10 (d, 1H, J=8.1 Hz), 8.17 (brs, 1H), 8.64 (d, 1H, J=8.1 Hz), 9.91 (brs, 1H).

REFERENCE EXAMPLE 14

(2S)-2-((((4-cyanophenyl)amino)thioxomethyl)amino)-4-methyl-N-((3S)-tetrahydro-2-oxo-3-furanyl)pentanamide (Reference Compound 14)

Operations in the same manner as in Reference Example 7 and using 4-cyanophenyl isothiocyanate instead of phenyl isothiocyanate afforded Reference Compound 14 as a white solid.

mp 71.9–73.4° C. $^1$H-NMR (300 MHz, DMSO-$d_6$)δ: 0.90 (d, 3H, J=6.1 Hz), 0.91 (d, 3H, J=6.1 Hz), 1.56–1.69 (m, 3H), 2.14–2.25 (m, 1H), 2.36–2.44 (m, 1H), 4.17–4.25 (m, 1H), 4.35 (dt, 1H, J=8.0, 1.7 Hz), 4.56–4.65 (m, 1H), 4.92 (dd, 1H, J=14.5, 7.5 Hz), 7.73 (d, 2H, J=8.5 Hz), 7.86 (d, 2H, J=8.7 Hz), 8.18 (d, 1H, J=8.1 Hz), 8.66 (d, 1H, J=8.1 Hz), 10.08 (brs, 1H).

REFERENCE EXAMPLE 15

(2S)-4-methyl-2-((((2-methylphenyl)amino)thioxomethyl)amino)-N-((3S)-tetrahydro-2-oxo-3-furanyl)pentanamide (Reference Compound 15)

Operations in the same manner as in Reference Example 7 and using 2-methylphenyl isothiocyanate instead of phenyl isothiocyanate afforded Reference Compound 15 as pale-yellow crystals.

$^1$H-NMR (300 MHz, DMSO-$d_6$)δ: 0.92 (d, 6H, J=6.3 Hz), 1.54–1.71 (m, 3H), 2.18 (s, 3H), 2.20 (m, 1H), 2.42 (m, 1H), 4.22 (m, 2H), 4.36 (m, 2H), 7.14–7.40 (m, 4H), 7.55 (d, 1H, J=8.1 Hz), 8.58 (d, 1H, J=8.1 Hz), 9.21 (s, 1H).

REFERENCE EXAMPLE 16

(2S)-4-methyl-2-((((3-methylphenyl)amino)thioxomethyl)amino)-N-((3S)-tetrahydro-2-oxo-3-furanyl)pentanamide (Reference Compound 16)

Operations in the same manner as in Reference Example 7 and using 3-methylphenyl isothiocyanate instead of phenyl isothiocyanate afforded Reference Compound 16 as a white solid.

mp 59.1–62.2° C. $^1$H-NMR (300 MHz, DMSO-$d_6$)δ: 0.86 (d, 3H, J=6.3 Hz), 0.91 (d, 3H, J=6.3 Hz), 1.51–1.72 (m, 2H), 2.10–2.25 (m, 1H), 2.27 (s, 3H), 2.33–2.44 (m, 1H), 4.15–4.25 (m, 1H), 4.30–4.38 (m, 1H), 4.54–4.65 (m, 2H), 4.92–4.99 (m, 1H), 6.91 (d, 1H, J=7.3 Hz), 7.18 (t, 1H, J=7.8 Hz), 7.30 (d, 1H, J=9.2 Hz), 7.31 (s, 1H), 7.72 (d, 1H, J=8.2 Hz), 8.61 (d, 1H, J=8.2 Hz), 9.62 (s, 1H).

REFERENCE EXAMPLE 17

(2S)-4-methyl-2-((((4-methylphenyl)amino)thioxomethyl)amino)-N-((3S)-tetrahydro-2-oxo-3-furanyl)pentanamide (Reference Compound 17)

Operations in the same manner as in Reference Example 7 and using 4-methylphenyl isothiocyanate instead of phenyl isothiocyanate afforded Reference Compound 17 as colorless crystals.

mp 107.9–111.2° C. $^1$H-NMR (300 MHz, DMSO-$d_6$)δ: 0.89 (d, 3H, J=6.5 Hz), 0.90 (d, 3H, J=6.5 Hz), 1.40–1.51 (m, 2H), 1.52–1.70 (m, 1H), 2.09–2.27 (m, 1H), 2.20 (s, 3H), 2.32–2.43 (m, 1H), 4.16–4.29 (m, 2H), 4.34 (dd, 1H, J=8.8, 7.5 Hz), 4.55–4.64 (m, 1H), 6.27 (d, 1H, J=8.6 Hz), 7.01 (d, 2H, J=8.2 Hz), 7.24 (d, 2H, J=8.4 Hz), 8.44 (s, 1H), 8.57 (d, 1H, J=8.2 Hz).

EXAMPLE 1

(2S)-4-methyl-2-(((phenylamino)thioxomethyl)amino)-N-((3S)-tetrahydro-2-hydroxy-3-furanyl)pentanamide (Compound 1)

Reference Compound 7 (1.7 g, 4.9 mmol) was dissolved in dichloromethane (200 mL) and 1M diisobutylaluminum hydride/toluene solution (17 mL, 17 mmol) was added at −78° C. This solution was stirred at −70° C. or below for 3 hr, saturated aqueous ammonium chloride solution (4.0 mL) was added and the mixture was stirred at room temperature for 30 min. Thereto were added anhydrous magnesium sulfate and ethyl acetate and inorganic matter was filtered off through celite. This filtrate was concentrated under reduced pressure and the residue was purified by HPLC (column; YMC-Pack ODS-A 250×20 mm I.D., eluent; acetonitrile/water/trifluoroacetic acid=30:70:0.1). The main fractions were collected and extracted with ethyl acetate. This solution was washed with saturated aqueous sodium hydrogen carbonate solution and saturated brine, dried over anhydrous magnesium sulfate, and concentrated under reduced pressure. The residue was crystallized from hexane to give Compound 1 (0.46 g, 27%) as colorless crystals.

mp 62.0–63.8° C. $^1$H-NMR (300 MHz, DMSO-$d_6$)δ: 0.91 (d, 6H, J=6.0 Hz), 1.49–1.91 (m, 4H), 2.14 (m, 1H), 3.64–4.00 (m, 3H), 4.91 (m, 1H), 5.00/5.11 (d/t, 1H, J=4.5/4.7 Hz), 6.16/6.34 (d/d, 1H, J=4.8/4.8 Hz), 7.10 (m, 1H), 7.29–7.34 (m, 2H), 7.49–7.53 (m, 2H), 7.72/7.78 (d/d, 1H, J=8.4/8.7 Hz), 8.26/7.87 (d/d, 1H, J=6.3/7.5 Hz), 9.69 (s,

1H), major:minor=1.0:0.85. MALDI-TOF MS [M+Na]$^+$ Calcd 358.174, Found 358.169. [α]$_D^{25}$ +23.6° (c=0.211).

EXAMPLE 2

(2S)-3-methyl-2-(((phenylamino)thioxomethyl)amino)-N-((3S)-tetrahydro-2-hydroxy-3-furanyl)pentanamide (Compound 2)

Operations in the same manner as in Reference Example 1 and using Reference Compound 8 instead of Reference Compound 7 afforded Compound 2 as colorless crystals.

mp 51.3–52.9° C. $^1$H-NMR (300 MHz, DMSO-d$_6$)δ: 0.81-0.87 (m, 6H), 1.03 (m, 1H), 1.48 (m, 1H), 1.68–1.86 (m, 2H), 2.11 (m, 1H), 3.48/3.86 (m/m, 1H), 3.91–3.96 (m, 2H), 4.88 (m, 1H), 4.99/5.10 (d/t, 1H, J=4.5/4.5 Hz), 6.13/6.27 (d/d, 1H, J=4.5/4.2 Hz), 7.07 (m, 1H), 7.27–7.32 (m, 2H), 7.49–7.52 (m, 2H), 7.70/7.71 (d/d, 1H, J=8.4/8.1 Hz), 7.85/8.21 (d/d, 1H, J=7.8/6.6 Hz), 9.76 (s, 1H), major:minor=1.0:0.77. MALDI-TOF MS [M+Na]$^+$ Calcd 374.151, Found 374.185. [≠]$_D^{25}$ +33.60 (c=0.208).

EXAMPLE 3

(2S)-3-methyl-2-(((phenylamino)thioxomethyl)amino)-N-((3S)-tetrahydro-2-hydroxy-3-furanyl)butanamide (Compound 3)

Operations in the same manner as in Example 1 and using Reference Compound 9 instead of Reference Compound 7 afforded Compound 3 as colorless crystals.

mp 50.9–51.9° C. $^1$H-NMR (300 MHz, DMSO-d$_6$)δ: 0.86–0.92 (m, 6H), 1.80 (m, 1H), 2.03–2.26 (m, 2H), 3.69/3.89 (m/m, 1H), 3.93–3.97 (m, 2H), 4.92 (m, 1H), 5.02/5.13 (d/t, 1H, J=4.5/4.7 Hz), 6.16/6.31 (d/d, 1H, J=4.5/4.8 Hz), 7.10 (m, 1H), 7.29–7.34 (m, 2H), 7.52–7.55 (m, 2H), 7.71 (m, 1H), 8.24/7.92 (d/d, 1H, J=6.6/7.5 Hz), 9.82 (s, 1H), major:minor=1.0:0.83. MALDI-TOF MS [M+Na]$^+$ Calcd 360.136, Found 360.137. [α]$_D^{25}$ +39.8° (c=0.201).

EXAMPLE 4

(2S)-2-(((benzylamino)thioxomethyl)amino)-4-methyl-N-((3S)-tetrahydro-2-hydroxy-3-furanyl)pentanamide (Compound 4)

Operations in the same manner as in Example 1 and using Reference Compound 10 instead of Reference Compound 7 afforded Compound 4 as colorless crystals.

mp 62.2–64.4° C. $^1$H-NMR (300 MHz, DMSO-d$_6$)δ: 0.84–0.89 (m, 6H), 1.44–1.82 (m, 4H), 2.14 (m, 1H), 3.68/4.03 (m/m, 2H), 3.85–3.97 (m, 2H), 4.66 (bs, 1H), 4.85 (m, 1H), 4.99/5.11 (d/t, 1H, J=4.5/4.4 Hz), 6.12/6.34 (d/bs, 1H, J=4.8 Hz), 7.22–7.36(m, 5H), 7.58 (m, 1H), 7.68/8.13 (bs, 1H), 7.96 (bs, 1H), major:minor=1.0:0.80. MALDI-TOF MS [M+Na]$^+$ $^{Calcd}$ 388.167, Found 388.162. [α]$_D^{25}$ +18.9° (c=0.211).

EXAMPLE 5

(2S)-2-((((4-fluorophenyl)amino)thioxomethyl)amino)-4-methyl-N-((3S)-tetrahydro-2-hydroxy-3-furanyl)pentanamide (Compound 5)

Operations in the same manner as in Example 1 and using Reference Compound 11 instead of Reference Compound 7 afforded Compound 5 as colorless crystals.

mp 77.2–78.3° C. $^1$H-NMR (300 MHz, DMSO-d$_6$)δ: 0.90 (d, 6H, J=6.3 Hz), 1.48–1.91 (m, 4H), 2.14 (m, 1H), 3.69/3.95 (m/m, 1H), 3.86–3.91 (m, 2H), 4.93 (m, 1H), 5.00/5.12 (d/t, 1H, J=5.1/4.5 Hz), 6.15/6.34 (d/d, 1H, J=4.8/3.9 Hz), 7.12–7.18 (m, 2H), 7.46–7.52 (m, 2H), 7.73/7.77 (d/d, 1H, J=8.1/7.8 Hz), 7.84/8.25 (d/d, 1H, J=7.8/7.2 Hz), 9.64 (s, 1H), major:minor=1.0:0.85. MALDI-TOF MS [M+Na]$^+$ Calcd 392.142, Found 392.141. [α]$_D^{25}$ +20.1° (c=0.199).

EXAMPLE 6

(2S)-2-((((4-methoxyphenyl)amino)thioxomethyl)amino)-4-methyl-N-((3S)-tetrahydro-2-hydroxy-3-furanyl)pentanamide (Compound 6)

Operations in the same manner as in Example 1 and using Reference Compound 12 instead of Reference Compound 7 afforded Compound 6 as colorless crystals.

mp 67.9–68.8° C. $^1$H-NMR (300 MHz, DMSO-d$_6$)δ: 0.88–0.91 (m, 6H), 1.47–1.87 (m, 4H), 2.14 (m, 1H), 3.69/3.94 (m/m, 1H), 3.74 (s, 3H), 3.86–3.90 (m, 2H), 4.89 (m, 1H), 4.99/5.11 (d/t, 1H, J=4.8/4.4 Hz), 6.15/6.35 (d/d, 1H, J=4.8/4.2 Hz), 6.88–6.91 (m, 2H), 7.28–7.33 (m, 2H), 7.47/7.53 (d/d, 1H, J=8.1/6.9 Hz), 8.22/7.81 (d/d, 1H, J=6.6/7.8 Hz), 9.49 (s, 1H), major:minor =1.0:0.78. MALDI-TOF MS [M+Na]$^+$ Calcd 404.162, Found 404.166. [α]$_D^{25}$ +19.9° (c=0.200).

EXAMPLE 7

(2S)-2-((((3-cyanophenyl)amino)thioxomethyl)amino)-4-methyl-N-((3S)-tetrahydro-2-hydroxy-3-furanyl)pentanamide (Compound 7)

Operations in the same manner as in Example 1 and using Reference Compound 13 instead of Reference Compound 7 afforded Compound 7 as colorless crystals.

mp 54.1–55.1° C. $^1$H-NMR (300 MHz, DMSO-d$_6$)δ: 0.90–0.92 (m, 6H), 1.45–1.90 (m, 4H), 2.15 (m, 1H), 3.69/3.96 (m/m, 1H), 3.86–3.91 (m, 2H), 4.93 (m, 1H), 5.01/5.12 (d/t, 1H, J=4.8/4.5 Hz), 6.16/6.34 (d/d, 1H, J=4.8/4.5 Hz), 7.48-7.54 (m, 2H), 7.75 (m, 1H), 8.06–8.18 (m, 2H), 8.30/7.92 (d/d, 1H, J=6.9/7.5 Hz), 9.93 (s, 1H), major:minor=1.0:0.75. MALDI-TOF MS [M+Na]$^+$ Calcd 399.147, Found 399.167. [α]$_D^{25}$ +23.80 (c=0.210).

EXAMPLE 8

(2S)-2-((((4-cyanophenyl)amino)thioxomethyl)amino)-4-methyl-N-((3S)-tetrahydro-2-hydroxy-3-furanyl)pentanamide (Compound 8)

Operations in the same manner as in Example 1 and using Reference Compound 14 instead of Reference Compound 7 afforded Compound 8 as colorless crystals.

mp 80.0–82.9° C. $^1$H-NMR (300 MHz, DMSO-d$_6$)δ: 0.89–0.92 (m, 6H), 1.50–1.90 (m, 4H), 2.14 (m, 1H), 3.69/3.96 (m/m, 1H), 3.86–3.91 (m, 2H), 4.93 (m, 1H), 5.01/5.12 (d/t, 1H, J=5.1/4.5 Hz), 6.16/6.33 (d/d, 1H, J=4.5/4.2 Hz), 7.73–7.76 (m, 2H), 7.84–7.88 (m, 2H), 8.18 (m, 1H), 8.31/7.95 (d/d, 1H, J=6.6/7.8 Hz), 10.10 (s, 1H), major:minor=1.0:0.75. MALDI-TOF MS [M+Na]$^+$ Calcd 399.147, Found 399.150. [α]$_D^{25}$ +51.2° (c=0.195).

EXAMPLE 9

(2S)-4-methyl-2-((((2-methylphenyl)amino)thioxomethyl)amino)-N-((3S)-tetrahydro-2-hydroxy-3-furanyl)pentanamide (Compound 9)

Operations in the same manner as in Example 1 and using Reference Compound 15 instead of Reference Compound 7 afforded Compound 9 as colorless crystals.

mp 57.9–58.9° C. $^1$H-NMR (300 MHz, DMSO-$d_6$)δ: 0.88–0.91 (m, 6H), 1.48–1.86 (m, 4H), 2.16 (m, 1H), 2.17 (s, 3H), 3.69/3.94 (m/m, 1H), 3.86–3.90 (m, 2H), 4.91 (m, 1H), 4.98/5.11 (d/t, 1H, J=4.5/4.5 Hz), 6.15/6.36 (d/d, 1H, J=4.8/3.9 Hz), 7.12–7.31 (m, 4H), 7.46/7.52 (d/d, 1H, J=8.4/9.9 Hz), 7.78/8.19 (d/d, 1H, J=7.2/6.6 Hz), 9.20 (s, 1H), major:minor=1.0:0.89. MALDI-TOF MS [M+Na]$^+$ Calcd 388.167, Found 388.176. $[\alpha]_D^{25}$ +9.8° (c=0.203).

EXAMPLE 10

(2S)-4-methyl-2-((((3-methylphenyl)amino)thioxomethyl)amino)-N-((3S)-tetrahydro-2-hydroxy-3-furanyl)pentanamide (Compound 10)

Operations in the same manner as in Example 1 and using Reference Compound 16 instead of Reference Compound 7 afforded Compound 10 as colorless crystals.

mp 61.4–61.9° C. $^1$H-NMR (300 MHz, DMSO-$d_6$)δ: 0.91 (d, 6H, J=6.3 Hz), 1.47–1.88 (m, 4H), 2.12 (m, 1H), 2.28 (s, 3H), 3.69/3.95 (m/m, 1H), 3.86–3.91 (m, 2H), 4.92 (m, 1H), 5.00/5.11 (d/t, 1H, J=4.8/4.5 Hz), 6.15/6.34 (d/d, 1H, J=4.8/4.5 Hz), 6.92 (m, 1H), 7.17–7.30 (m, 3H), 7.68/7.74 (d/d, 1H, J=8.4/7.8 Hz), 8.24/7.84 (d/d, 1H, J=6.6/7.5 Hz), 9.63 (s, 1H), major:minor=1.0:0.87. MALDI-TOF MS [M+Na]+ Calcd 388.167, Found 388.175. $[\alpha]_D^{25}$ +4.8° (c=0.208).

EXAMPLE 11

(2S)-4-methyl-2-((((4-methylphenyl)amino)thioxomethyl)amino)-N-((3S)-tetrahydro-2-hydroxy-3-furanyl)pentanamide (Compound 11)

Operations in the same manner as in Example 1 and using Reference Compound 17 instead of Reference Compound 7 afforded Compound 11 as colorless crystals.

mp 87.3–88.7° C. $^1$H-NMR (300 MHz, DMSO-$d_6$)δ: 0.89 (d, 6H, J=6.6 Hz), 1.36–1.85 (m, 4H), 2.14 (m, 1H), 2.21 (s, 3H), 3.68/3.94 (m/m, 1H), 3.85–3.90 (m, 2H), 4.28 (m, 1H), 4.98/5.10 (d/t, 1H, J=4.8/4.7 Hz), 6.14/6.33 (d/d, 1H, J=4.5/3.6 Hz), 6.24 (m, 1H), 7.01–7.03 (m, 2H), 7.23–7.26 (m, 2H), 8.19/7.84 (d/d, 1H, J=7.2/7.8 Hz), 8.46 (s, 1H), major:minor=1.0:0.46. MALDI-TOF MS [M+Na]$^+$ Calcd 388.167, Found 388.165. $[\alpha]_D^{25}$ +23.9° (c=0.209).

EXPERIMENTAL EXAMPLE 1

Determination of μ-calpain and m-calpain Inhibitory Activity

The μ-calpain and m-calpain inhibitory activities were determined according to the method described in a reference [Anal. Biochem. vol. 208, 387–392 (1993)]. To be specific, a reaction mixture (200 μL) containing 0.5 mg/mL casein, 50 mM Tris-HCl buffer (pH 7.4), 20 mM dithiothreitol and 0.03 enzyme unit of μ-calpain (derived from human erythrocyte, manufactured by Cosmo Bio Co., Ltd.) or m-calpain (derived from pig kidney, manufactured by Cosmo Bio Co., Ltd.), dimethyl sulfoxide solution (2.5 μL) containing various concentrations of a test drug and 20 mM aqueous calcium chloride solution (50 μL) were added to a 96 well plate. After reaction at 30° C. for 60 min, the reaction mixture (100 μL) was transferred to a different 96 well plate, and purified water (50 μL) and 50% Coomassie brilliant blue solution (100 μL) were added. The plate was left standing at room temperature for 15 min and absorbance at 595 nm was measured. Using a value, measured after treating in the same manner without a test drug, as a control and a value, obtained by adding 1 mM EDTA instead of 20 mM aqueous calcium chloride solution, as a blank value, an inhibitory rate was calculated from the following formula and the amount ($IC_{50}$) necessary for 50% inhibition was determined.

Inhibitory rate (%)={1−(measure value−blank value)/(control value−blank value)}×100

Test Results 1

The results thereof are shown in Table 2.

TABLE 2

| μ-calpain and m-calpain inhibitory activity of the compound of the present invention | | |
|---|---|---|
| Test drug | 50% enzyme inhibition concentration [$IC_{50}$ (μM)] | |
| (Compound No.) | μ-calpain | m-calpain |
| 1 | 0.086 | 0.19 |
| 2 | 0.60 | 1.7 |
| 3 | 0.63 | 1.9 |
| 4 | 0.15 | 0.24 |
| 5 | 0.15 | 0.20 |
| 6 | 0.22 | 0.17 |
| 7 | 0.26 | 0.12 |
| 8 | 0.14 | 0.25 |
| 9 | 0.24 | 0.34 |
| 10 | 0.18 | 0.17 |
| 11 | 0.91 | 1.2 |

As a result, the compound of the present invention showed a superior calpain inhibitory activity.

EXPERIMENTAL EXAMPLE 2

Lens Opacity Preventive Action in Rat Lens Culture

The lenses obtained from SD rats (5-week-old) were divided into 3 groups, and cultured as follows.

(1) For normal group, the lens was cultured in a basic culture solution [Eagle's serum-free minimum essential medium (MEM, GIBCO) containing 10% fetal bovine serum (FBS, GIBCO)] throughout the experiment period.

(2) For control group, the lens was cultured in a basic culture solution.

(3) For drug group, the lens was cultured in a culture solution wherein Compound 1 dissolved in ethanol had been added to a basic culture solution (drug added culture solution; concentration of Compound 1 in culture solution: 100 μM, concentration of ethanol: 0.5%).

For control group and drug group, a solution of calcium ionophore (A23187, manufactured by Calbiochem-Novabiochem) in ethanol (A23187 (1 mg) was dissolved in ethanol (955 μL)) was added to the culture solution 2 hr after culture to make the concentration of A23187 10 μM. After 24 hr, the medium was changed to a drug added culture solution for the drug group and to a basic culture solution for the control group. After culture for 4 days, observation under stereoscopic microscope was performed and the opacity (pixel) of the lens was measured using an image analyzer (NIH image 1.62) using computer.

Test Results 2

The results are shown in FIG. 1. The lens of the normal group was transparent. The lens of the control group was opacified white at the center. In the group added with Compound 1 (drug group), the opacity was significantly suppressed.

The above results suggest that Compound 1 of the present invention is effective for the prevention of opacity of the lens.

EXPERIMENTAL EXAMPLE 3

Aqueous Humor Penetration Test

The suspension of Formulation Example 4 to be mentioned later was instilled by 50 μL into the both eyes of Japanese white rabbits (body weight about 2 kg, purchased from Fukusaki Rabbit Union). At 0.25, 0.5, 1 and 3 hr after the instillation, the rabbits were sacrificed with pentobarbital and aqueous humor was recovered. Using a column switching system HPLC, the concentration of Compound 1 in the aqueous humor was measured.

Test Results 3

Figure 2:
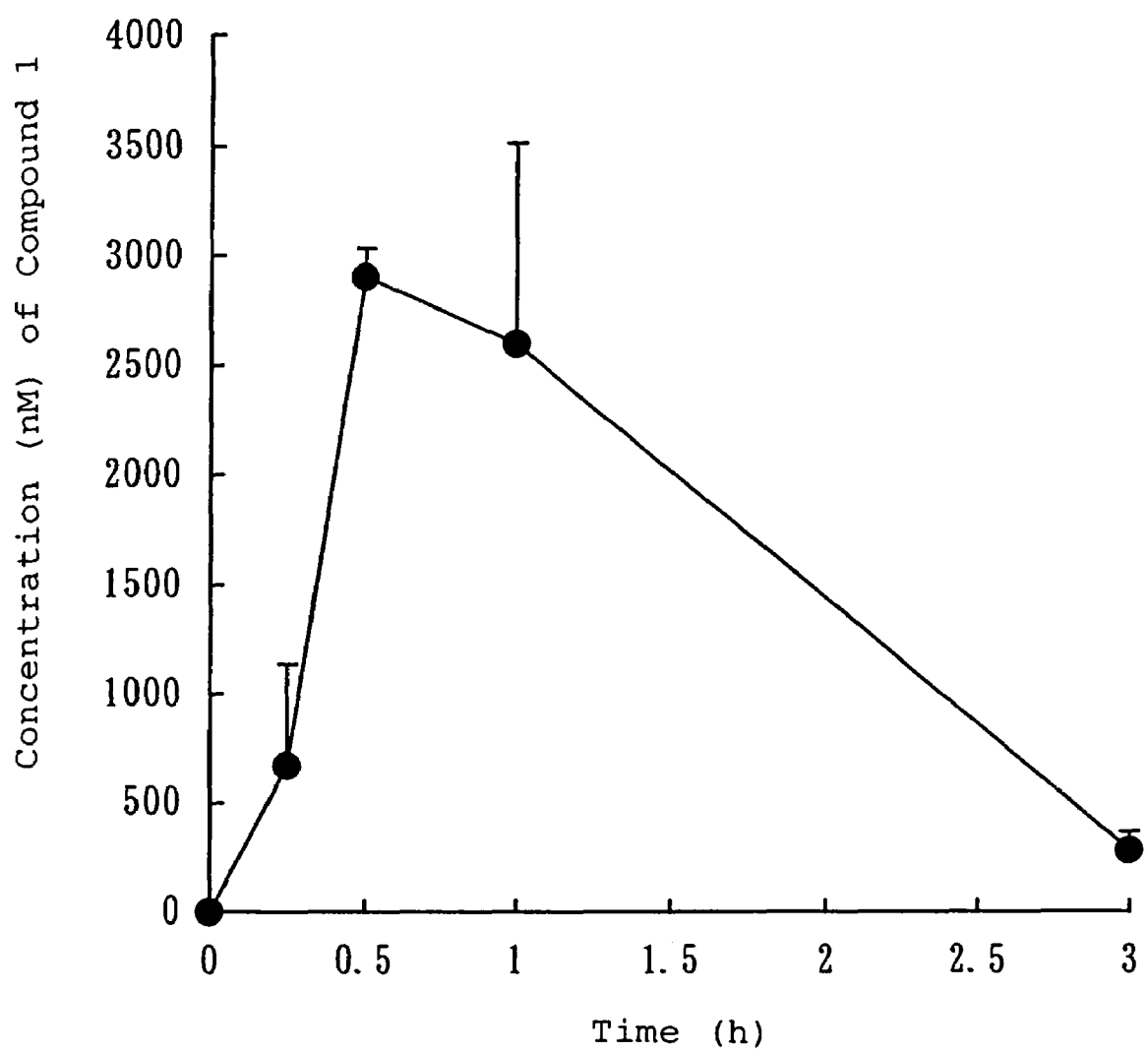
FIG. 2 is a graph showing the concentration of Compound 1 in aqueous humor after intraocular administration to rabbits, wherein each value shows mean±standard deviation (n=4).

The results thereof are shown in FIG. 2. The concentration of Compound 1 in the aqueous humor reached the maximum (Cmax) at 0.5 hr after the instillation and the concentration thereof was 2903.6 nM. The area under drug concentration—time curve (AUC) of the amount of Compound 1 penetrated to aqueous humor in 0-3 hr after the instillation was 4786.2 nM·h.

EXPERIMENTAL EXAMPLE 4

Effect on Rat Retinal Ischemic Disorder

Male SD rats (body weight: 150–200 g, purchased from Charles River Japan, Inc.) were used. For anesthesia, a mixture of equivalent amounts of 50 mg/mL ketamine injection and 20 mg/mL xylazine injection was administered intramuscularly at 1.0 mL/kg body weight into the femora of the rats 15 min before ischemia. To achieve ischemia, the optic nerve including central retinal artery was ligated using a Sugita Clip minitype (No. 98), and the blood flow was blocked for 55 min. For normal group, central retinal artery was only exposed and ischemia was not set up. After 7 days from reperfusion in ischemia, a tissue specimen was prepared. For preparation of the tissue specimen, an excess amount of pentobarbital solution was intraperitoneally administered to sacrifice the animal, and left eyeball was enucleated. The enucleated eyeball was fixed for 24 hr in a fixing solution of 2% paraformaldehyde and 2.5% glutaraldehyde (0.1 M phosphate buffer, pH 7.4). After fixing, a paraffin embedded block was prepared, sliced in a thickness of 3 μm at the section passing through the center of the optic disc and stained with hematoxylin and eosin (HE). Ganglion cells of retina per 0.25 mm width of the retina section at 1–2 mm from the center of the optic disc were counted under an optical microscope.

A solution obtained by dissolving sodium carboxycellulose in distilled water to a concentration of 0.5% (CMC solution) was orally administered to the control group, and a solution obtained by suspending Compound 1 in a CMC solution at 1.0%, such that Compound 1 was administered at 100 mg/kg body weight, was orally administered to the drug group, both at 15 min before start of ischemia and immediately after release from ischemia.

Test Results 4

Figure 3:
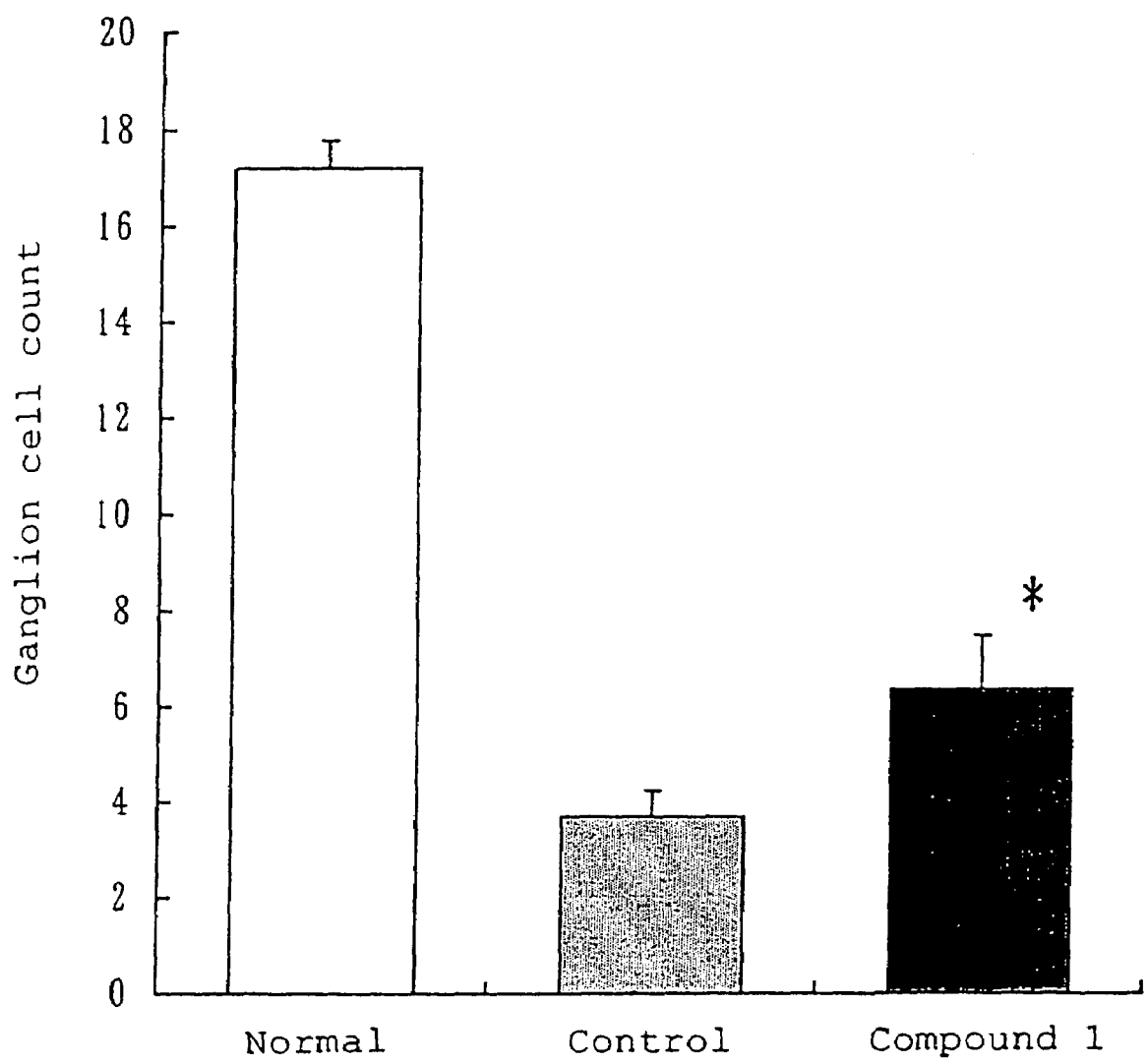
FIG. 3 is a graph showing a suppressive effect of Compound 1 on ganglion cell injury in rat retinal ischemia model, wherein each value shows mean±standard error (n=6), and * shows a significant difference p<0.05 from the control group by the Student's T test.

The results thereof are shown in FIG. 3. The ganglion cell count decreased to about ¼ of that of the normal group (control group) due to ischemia. In contrast, Compound 1 administration (drug group) significantly suppressed the decrease due to ischemia in the ganglion cell count.

The above results suggest that Compound 1 of the present invention has an effect to improve retinal ischemic disorder.

EXPERIMENTAL EXAMPLE 5

Cytotoxicity Test

Mouse neuroblastoma derived cell lines (N1E-115 cells) were seeded in a 96 well microplate at $10^4$ per well and cultured overnight in Dulbecco's Modified Eagle's Minimum Essential Medium (100 μL, DMEM, GIBCO) containing 10% FBS at 37° C. under 5% $CO_2$. The whole amount of the culture solution was removed, and the medium was changed to various concentrations of a test drug solution (100 μL, prepared by dissolving Compound 1 in 99.5% ethanol and adjusting final concentration of ethanol to 1% with DMEM) and the cells were cultured for 24 hr. The culture supernatant and cells were separately recovered. The cells were ultrasonicated to give soluble fractions and the lactic dehydrogenase (LDH) activity of each of them was determined with an LDH cytotoxicity detection kit (MK401, manufactured by Takara Bio Inc.), and an LDH release rate was determined by the following formula and taken as a proportion of the cells suffered from cytotoxicity.

LDH release rate (%)={$LDH$ activity of culture supernatant/($LDH$ activity of culture supernatant+intracellular $LDH$ activity)}×100

$LD_{50}$ was determined from the LDH release rate at each test drug concentration by $LD_{50}/ED_{50}$ probit method of SAS preclinical package (Ver. 6.12).

Test Results 5

The results thereof are shown in Table 3.

TABLE 3

| N1E-115 extracellularly released LDH | |
|---|---|
| concentration of test drug (Compound 1) | LDH release rate (%) |
| 0.1 mM | 9.32 ± 0.07 |
| 0.5 mM | 11.05 ± 0.72 |
| 1 mM | 14.22 ± 1.14 |
| 2 mM | 47.73 ± 1.66 |

$LD_{50}$ of Compound 1 as determined from the LDH release rate in Table 3 was 2.191±0.079 mM.

FORMULATION EXAMPLE 1

Tablet

| | |
|---|---|
| Compound 10 | 5 g |
| Starch | 12 g |
| Lactose | 27.2 g |
| Magnesium stearate | 0.4 g |

Compound 10, lactose and starch were thoroughly admixed to give granules for tableting according to a wet tablet preparation method. Magnesium stearate was added and the mixture was tableted to give 400 tablets. The tablets are coated with enteric coating agent (methacrylic acid copolymer), as necessary.

FORMULATION EXAMPLE 2

Injection

| Compound 5 | 100 mg |
| Sodium chloride | 900 mg |
| 1N Sodium hydroxide | suitable amount |
| Distillation water for injection | total amount 100 mL |

The above components are aseptically admixed by a conventional method to give an injection.

FORMULATION EXAMPLE 3

Eye Drop

| Compound 1 | 100 mg |
| Boric acid | 700 mg |
| Borax | suitable amount |
| Sodium chloride | 500 mg |
| Disodium edetate | 0.05 mg |
| Benzalkonium chloride | 0.0005 mg |
| Sterilized purified water | total amount 100 mL |

The above components are aseptically admixed by a conventional method to give an eye drop.

FORMULATION EXAMPLE 4

Eye Drop

| Compound 1 | 500 mg |
| Polysorbate 80 | 100 mg |
| Sodium dihydrogen phosphate dihydrate | 100 mg |
| Benzalkonium chloride | 5 mg |
| Sodium chloride | 900 mg |
| Sodium hydroxide | suitable amount |
| PH | 7.0 |
| Sterilized purified water | total amount 100 mL |

The above components are aseptically admixed by a conventional method to give an eye drop suspension.

INDUSTRIAL APPLICABILITY

Since the compound represented by the formula (I) of the present invention has a superior calpain inhibitory activity, it is useful as a drug for the prophylaxis or treatment of various diseases, in which calpain is involved, such as ischemic disease, immune disease, Alzheimer's disease, osteoporosis, disease arising from brain tissue disorder, cataract, glaucoma, retinochoroidal disease, complications of posterior segment of the eye arising from photocoagulation, a disease associated with angiogenesis and the like.

While some of the specific embodiments of this invention have been described in detail in the foregoing, it will be possible for those of ordinary skill in the art to variously modify and change the particular embodiments shown herein, within the scope not substantially deviating from the novel teaching and benefit of the invention. Accordingly, this invention encompasses all such modifications and changes within the spirit and scope of the invention as defined by the following claims.

This application is based on a patent application No. 2002-072762 filed in Japan, the contents of which are hereby incorporated by reference.

The invention claimed is:

1. A compound represented by the formula (I)

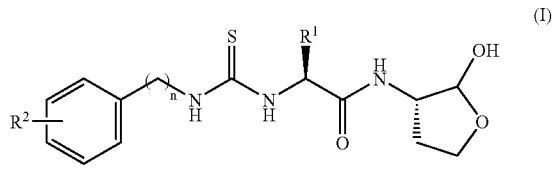

wherein $R^1$ is a lower alkyl group, $R^2$ is a hydrogen, a halogen, a cyano group, a lower alkyl group or a lower alkoxy group, and n is 0 or 1.

2. The compound of claim 1, wherein $R^1$ is a lower alkyl group having 3 or 4 carbon atoms.

3. The compound of claim 1, wherein $R^1$ is a group selected from isopropyl, isobutyl and sec-butyl.

4. The compound of claim 1, wherein $R^1$ is isobutyl and $R^2$ is a group selected from a hydrogen, a halogen, a cyano group, a lower alkyl group and a lower alkoxy group.

5. (2S)-4-Methyl-2-(((phenylamino)thioxomethyl)amino)-N-((3 S)-tetrahydro-2-hydroxy-3-furanyl) pentanamide.

6. A pharmaceutical composition comprising a compound represented by the formula (I)

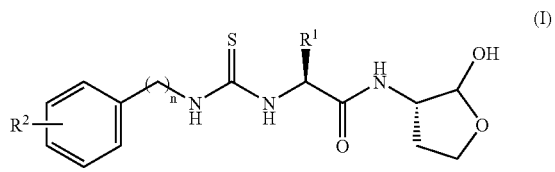

wherein $R^1$ is a lower alkyl group, $R^2$ is a hydrogen, a halogen, a cyano group, a lower alkyl group or a lower alkoxy group, and n is 0 or 1, and a pharmaceutically acceptable carrier.

7. A method for treating cataract or retinal ischemic disorder, which comprises administering an effective amount of a compound represented by the formula (I)

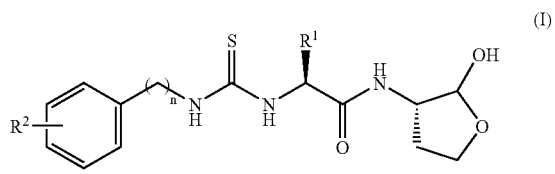

wherein $R^1$ is a lower alkyl group, $R^2$ is a hydrogen, a halogen, a cyano group, a lower alkyl group or a lower alkoxy group and n is 0 or 1, to a mammal in need of a treatment.

8. The compound of claim 2, wherein $R^1$ is a group selected from isopropyl, isobutyl and sec-butyl.

* * * * *